(12) United States Patent
Basu et al.

(10) Patent No.: US 12,197,864 B2
(45) Date of Patent: Jan. 14, 2025

(54) SYSTEM AND METHOD FOR INTELLIGENT DEFECT ANALYSIS

(71) Applicant: CERNER INNOVATION, INC., Kansas City, KS (US)

(72) Inventors: Soumya Basu, Parganas (IN); Anindya Deb, Kolkata (IN); Priyam Dey, Kolkata (IN); Rahul Dey, Kolkata (IN); Soumit Ghosh, Saltlake (IN); Rahul Paul, Kolkata (IN)

(73) Assignee: CERNER INNOVATION, INC., Kansas City, KS (US)

( * ) Notice: Subject to any disclaimer, the term of this patent is extended or adjusted under 35 U.S.C. 154(b) by 818 days.

(21) Appl. No.: 17/087,725

(22) Filed: Nov. 3, 2020

(65) Prior Publication Data

US 2021/0200950 A1 Jul. 1, 2021

Related U.S. Application Data

(60) Provisional application No. 62/954,031, filed on Dec. 27, 2019.

(51) Int. Cl.
| | | |
|---|---|---|
| G06F 40/289 | (2020.01) | |
| G06F 40/20 | (2020.01) | |
| G06F 40/279 | (2020.01) | |
| G06Q 10/0637 | (2023.01) | |
| G06Q 10/10 | (2023.01) | |
| G16H 10/60 | (2018.01) | |
| G16H 40/20 | (2018.01) | |
| G16H 50/20 | (2018.01) | |
| H04L 51/02 | (2022.01) | |
| G06F 3/04842 | (2022.01) | |

(52) U.S. Cl.
CPC ........... *G06F 40/289* (2020.01); *G06F 40/20* (2020.01); *G06F 40/279* (2020.01); *G06Q 10/06375* (2013.01); *G06Q 10/10* (2013.01); *G16H 10/60* (2018.01); *G16H 40/20* (2018.01); *G16H 50/20* (2018.01); *H04L 51/02* (2013.01); *G06F 3/04842* (2013.01)

(58) Field of Classification Search
CPC ........ G06F 40/289; G06F 40/20; G16H 10/60
See application file for complete search history.

(56) References Cited

U.S. PATENT DOCUMENTS

| | | | |
|---|---|---|---|
| 10,413,238 B1 * | 9/2019 | Cooper | A61B 5/1118 |
| 10,616,072 B1 * | 4/2020 | Lo | H04L 41/145 |
| 2011/0066893 A1 * | 3/2011 | Bassin | G06F 8/20 |
| | | | 714/E11.217 |

(Continued)

*Primary Examiner* — Bryan S Blankenagel
(74) *Attorney, Agent, or Firm* — Kilpatrick Townsend & Stockton

(57) ABSTRACT

Methods, systems, and computer-readable media are disclosed herein for intelligent defect analysis. In an aspect, a client environment is monitored for defects. Upon detecting and identifying a defect, the defect is analyzed using natural language processing in order to identify one or more keywords associated with the system defect. A historical record associated with the one or more keywords is identified and one or more solutions associated with the historical record are identified based on the keywords. The keywords and associated solutions may then be displayed as a notification on a graphical user interface.

20 Claims, 14 Drawing Sheets

(56) References Cited

U.S. PATENT DOCUMENTS

| | | | |
|---|---|---|---|
| 2011/0296244 A1* | 12/2011 | Fu | G06F 11/3608 |
| | | | 714/E11.029 |
| 2015/0278526 A1* | 10/2015 | Bhattacharya | G06F 11/3692 |
| | | | 726/1 |
| 2018/0285437 A1* | 10/2018 | Boggio | G06F 16/36 |
| 2019/0036849 A1* | 1/2019 | Uppala | H04L 51/02 |
| 2019/0340527 A1* | 11/2019 | Liden | G06F 3/04817 |
| 2019/0347282 A1* | 11/2019 | Cai | G06N 5/022 |
| 2020/0159991 A1* | 5/2020 | Chittari | G06F 3/04847 |
| 2020/0293946 A1* | 9/2020 | Sachan | G06N 5/04 |
| 2021/0174221 A1* | 6/2021 | Vijapur Gopinath Rao | |
| | | | G06N 20/00 |
| 2021/0174371 A1* | 6/2021 | Yoffe | G06V 20/20 |

* cited by examiner

FIG. 6

| | A<br>Clients | B<br>Records:<br>2 - 7 days | C<br>Requests:<br>2 - 7 days | D<br>Amount<br>$ | E<br>Records:<br>8 - 15 days | F<br>Requests:<br>8 - 15 days | G<br>Amount<br>$ | H<br>Records:<br>16 - 30 days | Total($) |
|---|---|---|---|---|---|---|---|---|---|
| 2 | Hospital 1 | | 0 X | 0 | 0 | 0 X | 0 | 0 | 0.02 |
| 3 | Hospital 2 | | 0 X | 0 | 0 | 0 X | 0 | 0 | |
| 4 | Hospital 3 | | 0 X | 0 | 0 | 0 X | 0 | 0 | 1214.00 |
| 5 | Hospital 4 | | 0 X | 0 | 0 | 0 X | 0 | 0 | |
| 6 | Hospital 5 | | 0 X | 0 | 0 | 0 X | 0 | 0 | 0.00 |
| 7 | Hospital 6 | | 0 X | 0 | 0 | 0 X | 0 | 0 | |
| 8 | Hospital 7 | | 0 X | 0 | 0 | 0 X | 0 | 0 | 0.00 |
| 9 | Hospital 8 | | 0 X | 0 | 0 | 0 X | 0 | 0 | |
| 10 | Hospital 9 | | 0 X | 0 | 0 | 1 2054120251050 X | 0 | 0 | |
| 11 | Hospital 10 | | 0 X | 0 | 0 | 0 X | 0 | 0 | |
| 12 | Hospital 11 | | 0 X | 0 | 0 | 0 X | 0 | 0 | |
| 13 | Hospital 12 | | 0 X | 0 | 0 | 0 X | 0 | 0 | |
| 14 | Hospital 13 | | 0 X | 0 | 0 | 0 X | 0 | 0 | |
| 15 | Hospital 14 | | 0 4450970672070 X | 4369.83 | 14 4379867398560 X | 6844.29 | 41 | | 178795.00 |
| 16 | Hospital 15 | | 0 X | 0 | 0 | 0 X | 0 | 0 | 4105.67 |
| 17 | Hospital 16 | | 0 X | 0 | 0 | 0 X | 0 | 0 | |
| 18 | Hospital 17 | | 35 1738652480830 X | 19087.1 | 35 1738625049400 X | 19449.6 | 33 | | 1093232.60 |
| 19 | Hospital 18 | | 0 X | 0 | 0 | 0 X | 0 | 0 | 1576.21 |
| 20 | Hospital 19 | | 0 X | 0 | 0 | 0 X | 0 | 0 | |
| 21 | Hospital 20 | | 0 X | 0 | 0 | 0 X | 0 | 0 | 0.00 |
| 22 | Hospital 21 | | 0 X | 0 | 0 | 0 X | 0 | 0 | |
| 23 | Hospital 22 | | 0 X | 0 | 0 | 0 X | 0 | 0 | 0.00 |
| 24 | Hospital 23 | | 0 X | 0 | 0 | 0 X | 0 | 0 | |
| 25 | Hospital 24 | | 0 X | 0 | 0 | 0 X | 0 | 0 | |
| 26 | Hospital 25 | | 0 X | 0 | 0 | 0 X | 0 | 0 | |
| 27 | Hospital 26 | | 0 X | 0 | 0 | 0 X | 0 | 0 | |
| 28 | Hospital 27 | | 0 X | 0 | 0 | 0 X | 0 | 0 | |
| 29 | Hospital 28 | | 0 X | 0 | 0 | 0 X | 0 | 0 | |
| 30 | Hospital 29 | | 0 X | 0 | 0 | 0 X | 0 | 0 | |
| 31 | Hospital 30 | | 0 X | 0 | 0 | 0 X | 0 | 0 | |
| 32 | Hospital 31 | | 0 X | 0 | 0 | 0 X | 0 | 0 | |
| 33 | Hospital 32 | | 4 1424949144 80 X | 0 | 0 | 4 1383669605900 X | 0 | 4 | |
| 34 | Hospital 33 | | 0 X | 0 | 0 | 0 X | 0 | 0 | |
| 35 | Hospital 34 | | 0 X | 0 | 0 | 0 X | 0 | 0 | |
| 36 | Hospital 35 | | 0 X | 0 | 0 | 0 X | 0 | 0 | |

| Receivable | Claims | GuarantorAccount | StatementRequest | PaymentAgreement | SBO |
|---|---|---|---|---|---|
| $1.6M | $2.7M | $0 | $0 | $0 | $32.8K |

Reimbursement: $163.3K

SF-Clients:
Hospital 1
Hospital 2
Hospital 3
Hospital 3
Hospital 3
Hospital 3
Hospital 3
Hospital 3
Hospital 3

Rev Impact Report
Filter By SF Clients...
Showing 1 to 10 of 64 entries
Show 10 entries Master Report
Clear Filters
Print
Print

600

SYSTEM AND METHOD FOR INTELLIGENT DEFECT ANALYSIS

CROSS REFERENCE TO RELATED APPLICATION

This application claims the benefit of priority under 35 U.S.C. § 119(e) to the filing date of U.S. Provisional Patent Application 62/954,031, filed on 27 Dec. 2019, entitled, "Intelligent Defect Analysis," which is incorporated by reference herein in its entirety.

BACKGROUND

Identification of defects is an essential part of support processes. Software support is available to help detect deviances and anomalies in critical business processes. For instance, revenue processing is essential for an entity as it is required to collect revenue. Processing of claims data, for example, should be performed and completed so that a user may bill another party for services or products provided, and subsequently receive accurate and timely payments based on the bill. At best, current support systems are limited to monitoring that is only reactive, such that a client identifies an issue and reports it to the system and the system then investigates to identify the cause of the issue.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims as supported by the Specification, including the Detailed Description and Drawings.

In brief and at a high level, embodiments of the present invention provide systems, methods, and computer-readable media for intelligent defect analysis. Embodiments provide an application and/or cloud-based service that intelligently identifies defects prior to the system being notified by a client or external third party. The intelligent defect analysis tool can proactively monitor a client environment to identify a resolution before a client identifies a defect.

One aspect of the present disclosure relates to a method for providing intelligent defect analysis. In aspects, a client environment is periodically monitored. A system defect is identified based on the monitoring of the client environment. In aspects, based on identifying the system defect, natural language processing is performed to analyze the system defect, wherein the natural language processing identifies one or more keywords associated with the system defect. A historical record associated with the one or more keywords is identified. One or more solutions associated with the historical record are identified based on the one or more keywords. In some aspects display of a notification is caused on a graphical user interface, wherein the notification includes at least one of: the one or more keywords or the one or more solutions.

In another aspect, the present disclosure relates to non-transitory computer-storage media having computer-executable instructions embodied thereon that, when executed, perform a method of providing intelligent defect analysis. In aspects, a client environment is periodically monitored. A system defect is identified based on the monitoring of the client environment. In aspects, based on identifying the system defect, intelligent natural language processing is performed to analyze the system defect, wherein the intelligent natural language processing identifies one or more keywords associated with the system defect. A plurality of historical records associated with the one or more keywords is identified. One or more solutions associated with the plurality of historical records are identified based on the one or more keywords, or the one or more solutions. In some aspects, display of a notification is caused on a graphical user interface of a user computing device, wherein the notification includes at least one of: the one or more keywords or the one or more solutions.

In yet another aspect, the present disclosure relates to a system for providing intelligent defect analysis. The system includes, a hardware processor configured to perform operations in response to receiving an instruction selected from a predefined native instruction set of codes, a memory, and a database configured to store a plurality of historical records. In some aspects, the system includes a proactive monitoring component configured to: periodically monitor a client environment, and identify a system defect based on the monitoring of the client environment. In further aspects, the system includes an analysis component configured to perform natural language processing to analyze the system defect, wherein the natural language processing identifies one or more keywords associated with the system defect. In further embodiments, the analysis component is also configured to identify one or more of the plurality of historical records in the database as being associated with the one or more keywords. In embodiments, the system also includes an action framework component configured to identify one or more solutions associated with the one or more of the plurality of historical records and the one or more keywords. In further embodiments, the system also includes a display component configured to cause display of a notification on a graphical user interface, wherein the notification includes at least one of the one or more keywords or the one or more solutions.

BRIEF DESCRIPTION OF THE DRAWINGS

Embodiments are described in detail below with reference to the attached drawings figures, wherein:

FIG. 6 illustrates a graphical user interface that presents output of the monitoring component of FIG. 5, in accordance with an embodiment of the present disclosure;

DETAILED DESCRIPTION

Figure 1A:
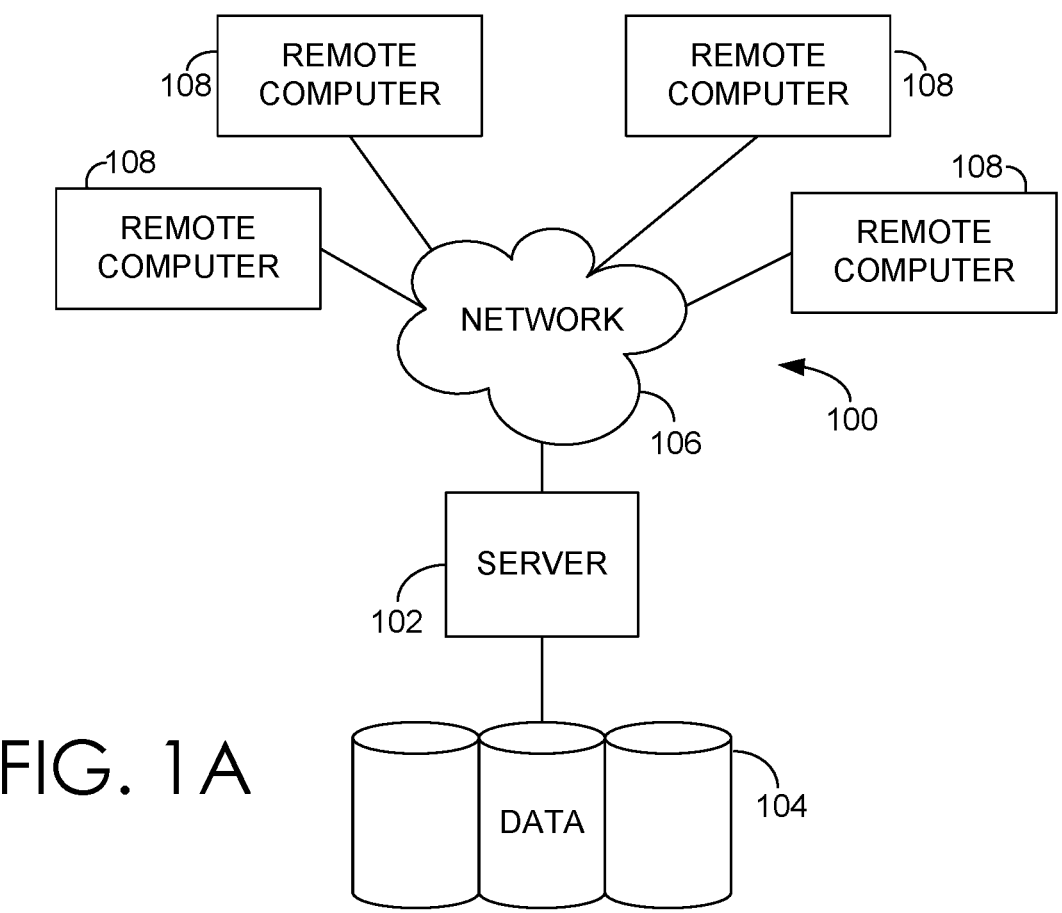
FIGS. 1A and 1B depict an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the disclosure may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-useable instructions embodied on one or more computer-readable media, as discussed further herein.

At a high level, embodiments of the present invention provide intelligent defect analysis. The software product can communicate with one or more disparate sources to, among other things, access data from, for example, an EHR (electronic health record) system, store health data in an EHR system, identify one or more defects, generate one or more action items, and the like. The software product can provide the integration with an EHR system while preserving privacy of an individual and the data associated therewith accessed from the EHR system.

Initially, there are five main components of the present tool: proactive monitoring, assistance, analysis, investigation, and action. Each will be discussed herein. While these five components are discussed herein, the present solution is not limited to these five components as additional components can be integrated into the tool to perform the same or different functions. Additionally, any of the five components discussed herein can be integrated into other components such that a single component can perform the functions of what is described herein as being performed by more than one component.

The proactive monitoring component provides a framework that proactively monitors a client environment. A client environment, as used herein, refers generally to an environment that is external to the present tool or managed by a third-party. The tool has the ability to integrate multiple custom tools to proactively monitor client environments to identify action items for resolution prior to a client identifying the presence of an issue/defect. The proactive monitoring component can be configured to only monitor non-protected health information (PHI) data.

The proactive monitoring component can monitor a client environment to identify one or more defects or a potential for one or more defects. In the previous revenue system example, the proactive monitoring component can, for instance, identify unprocessed revenue prior to a client indicating the presence of unprocessed revenue. Defects can be configurable by a client or any other authorized user. As later discussed herein, for example, FIG. 6 illustrates an example of output from a monitoring component, which illustrates a plurality of clients (column A) with, potentially, unprocessed revenue. Line 15, column H, for example, illustrates there are 41 unprocessed revenue items. Clicking on the '41' can navigate a user to a screen including each of the 41 items.

The proactive monitoring component can run in the background of a client environment and can continuously monitor the environment or perform periodic monitoring checks and predetermined intervals of time (e.g., monitoring checks every hour, every two hours, etc.).

When the proactive monitoring component identifies one or more defects, an alert is generated indicating the presence of the one or more defects. The alert can be an audible alert, a visual alert, or a combination thereof. The alert can include the defect present and any information related thereto.

The assistance component can assist with repetitive, well-defined problems with known solutions. The assistance component can leverage existing knowledge (e.g., knowledge bases) for well-defined problems and solutions (e.g., configuration issues, deployment issues, client environment issues, etc.). A well-defined or recurring problem is a defect that has been detected a number of times greater than a predetermined threshold number of times.

The assistance component can include a "chatbot" to assist with identifying a solution to recurring problems. The chatbot is helpful for identifying solutions to known problems. For instance, if a user queries the system for a guide/job, the system can return a link to open the guide/job using the chatbot.

The analysis component can identify possible problems and possible solutions for one or more defects. A defect can be identified (e.g., a client can provide a defect number) and the problem and potential solution for that defect can be identified. The analysis component can further identify similar defects and solutions thereof. Similar defects can be identified by utilizing algorithms to identify a nearest match to the identified defect/issue. Keywords, for example, can be used to identify similar defects. The keywords can be identified from unstructured, free text. The analysis component can perform pre-processing where text is cleaned up and keywords are identified therein so that the identified keywords can be matched with keywords in identified defects from, for example, a defect database or data store to identify a nearest possible solution.

The analysis component can use an intelligent natural language processing system to identify actionable insights from historical records to identify a solution to an existing problem. This is a step towards creating a self-healing system. This capability assists to analyze any defect without prior domain and technical expertise. All historical records documented in a defect tracking system is analyzed to find probable causes for the present issue with possible resolutions.

Once identified, an investigation component can be utilized to narrow down possible causes to probable or actual causes. One or more tools can be used in a client environment to identify one or more criteria for a cause and identify if the criteria is met. For instance, if an issue is identified as being similar by the analysis component and the similar issue is caused by a server being out of space, the investigation component can investigate the client environment to identify if the server associated with the current defect is actually out of space. If yes, this could possibly be the cause.

If not, this possible cause can be eliminated as it is not the actual cause. In other words, the criteria for the defect/solution has not been met (e.g., the server is not actually out of space so a defect cause based on a server being out of space cannot be the issue). The tool can utilize machine learning to learn from feedback. In other words, if a user consistently rejects a similar suggested issue for a defect then the system can stop providing that as a suggestion.

Finally, the action framework can assist in providing prescriptive or corrective action plans for driving the defect resolution. In other words, the identified solution can be mapped to solution steps and the execution of these steps can be automated. As the system has identified the likely issue (by the investigation component), the correct recommendation to fix the issue can be recommended.

The present tool can also generate an impact analysis report illustrating all other areas impacted by the defect. This can help to identify any other areas that may need to be changed or updated and identify areas where the code is called. This is helpful for integration testing to make sure that a defect is fixed before introduced to other areas of the environment.

An exemplary impact analysis summarization report that can be utilized as free text to identify potential actionable insights is provided as FIGS. 8-13. For example, as later discussed with regard to FIG. 11, it can be seen that the server was rebooted due to OS patch installation to fix the issue. A user, in the below, searched for the defect identified as "10343". It was provided along with a plurality of similar defects. Any one of the defects can be selected to provide a summarization of defect screen, as shown in the graphical user interfaces of FIGS. 8-13 where defect "10343" was selected and a defect summary screen for the defect identified as 10343 was provided.

This platform can provide a framework to forecast anomalies, analyze probable causes, provide assistance on preventative actions, plug in investigative tools to drive system driven resolution, and the like. Historical information from defect tracking systems can be leveraged to quickly identify similar defects and actionable insights or recommendations to resolve a defect.

A computing environment is described with regard to the systems, methods, and computer-media described hereinabove. Turning to FIG. 1A, one example of a computing environment 100 is depicted, in accordance with an embodiment of the present invention. It will be understood by those of ordinary skill in the art that the computing environment 100 is just one example of a suitable computing environment and is not intended to limit the scope of use or functionality of the present invention. Similarly, the computing environment 100 should not be interpreted as imputing any dependency and/or any requirements with regard to each component and combination(s) of components illustrated in FIG. 1A. It will be appreciated by those having ordinary skill in the art that the connections illustrated in FIG. 1A are also exemplary as other methods, hardware, software, and devices for establishing a communications link between the components, devices, systems, and entities, as shown in FIG. 1A, may be utilized in implementation of the present invention. Although the connections are depicted using one or more solid lines, it will be understood by those having ordinary skill in the art that the connections of FIG. 1A may be hardwired or wireless, and may use intermediary components that have been omitted or not included in FIG. 1A for simplicity's sake. As such, the absence of components from FIG. 1A should be not be interpreted as limiting the present invention to exclude additional components and combination(s) of components. Moreover, though devices and components are represented in FIG. 1A as singular devices and components, it will be appreciated that some embodiments may include a plurality of the devices and components such that FIG. 1A should not be considered as limiting the number of a device or component.

Continuing, the computing environment 100 of FIG. 1A is illustrated as being a distributed environment where components and devices may be remote from one another and may perform separate tasks. The components and devices may communicate with one another and may be linked to each other using a network 106. The network 106 may include wireless and/or physical (e.g., hardwired) connections. Exemplary networks include a telecommunications network of a service provider or carrier, Wide Area Network (WAN), a Local Area Network (LAN), a Wireless Local Area Network (WLAN), a cellular telecommunications network, a Wi-Fi network, a short range wireless network, a Wireless Metropolitan Area Network (WMAN), a Bluetooth® capable network, a fiber optic network, or a combination thereof. The network 106, generally, provides the components and devices access to the Internet and web-based applications.

The computing environment 100 comprises a computing device 102 shown in the form of a server. Although illustrated as one component in FIG. 1A, the present invention may utilize a plurality of local servers and/or remote servers in the computing environment 100. The computing device 102 may include components such as a processing unit, internal system memory, and a suitable system bus for coupling to various components, including a data store, database, or data store/database cluster. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The computing device 102 may include or may have access to computer-readable media. Computer-readable media can be any available media that may be accessed by computing device 102, and includes volatile and nonvolatile media, as well as removable and non-removable media. By way of example, and not limitation, computer-readable media may include computer storage media and communication media. Computer storage media may include, without limitation, volatile and nonvolatile media, as well as removable and non-removable media, implemented in any method or technology for storage of information, such as computer-readable instructions, data structures, program modules, or other data. In this regard, computer storage media may include, but is not limited to, Random Access Memory (RAM), Read-Only Memory (ROM), Electrically Erasable Programmable Read-Only Memory (EEPROM), flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the computing device 102. Computer storage media does not comprise signals per se.

Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, radio frequency (RF), infrared, and other wireless media. Combinations of any of the above also may be included within the scope of computer-readable media.

In embodiments, the computing device 102 uses logical connections to communicate with one or more remote computers 108 within the computing environment 100. In embodiments where the network 106 includes a wireless network, the computing device 102 may employ a modem to establish communications with the Internet, the computing device 102 may connect to the Internet using Wi-Fi or wireless access points, or the server may use a wireless network adapter to access the Internet. The computing device 102 engages in two-way communication with any or all of the components and devices illustrated in FIG. IA, using the network 106. Accordingly, the computing device 102 may send data to and receive data from the remote computers 108 over the network 106.

Although illustrated as a single device, the remote computers 108 may include multiple computing devices. In an embodiment having a distributed network, the remote computers 108 may be located at one or more different geographic locations. In an embodiment where the remote computers 108 is a plurality of computing devices, each of the plurality of computing devices may be located across various locations such as buildings in a campus, medical and research facilities at a medical complex, offices or "branches" of a banking/credit entity, or may be mobile devices that are wearable or carried by personnel, or attached to vehicles or trackable items in a warehouse, for example.

In some embodiments, the remote computers 108 is physically located in a medical setting such as, for example, a laboratory, inpatient room, an outpatient room, a hospital, a medical vehicle, a veterinary environment, an ambulatory setting, a medical billing office, a financial or administrative office, hospital administration setting, an in-home medical care environment, and/or medical professionals' offices. By way of example, a medical professional may include physicians; medical specialists such as surgeons, radiologists, cardiologists, and oncologists; emergency medical technicians; physicians' assistants; nurse practitioners; nurses; nurses' aides; pharmacists; dieticians; microbiologists; laboratory experts; genetic counselors; researchers; veterinarians; students; and the like. In other embodiments, the remote computers 108 may be physically located in a non-medical setting, such as a packing and shipping facility or deployed within a fleet of delivery or courier vehicles.

Continuing, the computing environment 100 includes a data store 104. Although shown as a single component, the data store 104 may be implemented using multiple data stores that are communicatively coupled to one another, independent of the geographic or physical location of a memory device. Exemplary data stores may store data in the form of artifacts, server lists, properties associated with servers, environments, properties associated with environments, computer instructions encoded in multiple different computer programming languages, deployment scripts, applications, properties associated with applications, release packages, version information for release packages, build levels associated with applications, identifiers for applications, identifiers for release packages, users, roles associated with users, permissions associated with roles, workflows and steps in the workflows, clients, servers associated with clients, attributes associated with properties, audit information, and/or audit trails for workflows. Exemplary data stores may also store data in the form of electronic records, for example, electronic medical records of patients, transaction records, billing records, task and workflow records, chronological event records, and the like.

Generally, the data store 104 includes physical memory that is configured to store information encoded in data. For example, the data store 104 may provide storage for computer-readable instructions, computer-executable instructions, data structures, data arrays, computer programs, applications, and other data that supports the functions and action to be undertaken using the computing environment 100 and components shown in exemplary FIG. 1A.

In various embodiments, the computing device 102, the one or more remote computers 108, and/or the data store 104 may be "sources" or "source devices," terms that are used interchangeably hereinafter. A source device can comprise any type of computing device capable of use by a user. By way of example and not limitation, a source device can be embodied as a personal computer (PC), a laptop computer, a mobile device, a smartphone, a tablet computer, a smart watch, a wearable computer, a fitness tracker, a personal digital assistant (PDA) device, a global positioning system (GPS) device, a video player, a handheld communications device, an embedded system controller, a camera, a remote control, a wearable electronic device with a camera (e.g., smart glasses, gesture-based wearable computers, etc.) a consumer electronic device, a workstation, or any combination of these delineated devices, a combination of these devices, or any other suitable computer device. The source device, as applied herein, can be utilized to access, for instance, the cloud-based solution to request creation of the item.

For example, one or more source devices may be an EHR server or any system that maintains, and provides access to, one or more EHR data store(s) containing records of treatment events, medication history, diagnoses, problems, allergies, demographic attributes, laboratory tests, time and date data, and any other health-related data, or any combination thereof for a plurality of patients. Additionally, the source devices can include clinical notes, appointment notes, records of issued prescriptions, diagnoses, care plans, bloodwork, urinalysis, treatment data, emergency contact information, and the like, for each patient of a healthcare facility or a plurality of healthcare facilities. Further, source devices can include images, representations, or clinical documentation of physical health data (e.g., X-rays, CT scans, ultrasound images, etc.). Additionally, in some embodiments, source devices can maintain one or more pharmaceutical formularies that identify prescriptions prescribed by, or available for prescription by, care providers.

In a computing environment having distributed components that are communicatively coupled via the network 106, program modules may be located in local and/or remote computer storage media including, for example only, memory storage devices. Embodiments of the present invention may be described in the context of computer-executable instructions, such as program modules, being executed by a computing device. Program modules may include, but are not limited to, routines, programs, objects, components, and data structures that perform particular tasks or implement particular abstract data types. In embodiments, the computing device 102 may access, retrieve, communicate, receive, and update information stored in the data store 104, including program modules. Accordingly, the computing device 102 may execute, using a processor, computer instructions stored in the data store 104 in order to perform embodiments described herein.

Although internal components of the devices in FIG. 1A, such as the computing device 102, are not illustrated, those of ordinary skill in the art will appreciate that internal components and their interconnection are present in the devices of FIG. 1A. Accordingly, additional details concerning the internal construction device are not further disclosed herein.

It should also be understood that the computing environment 100 shown in FIG. 1A is an example of one suitable computing system architecture. Each of the components of FIG. 1A may be implemented via any type of computing device. The components can communicate with each other via a network including, without limitation, one or more local area networks (LANs) and/or wide area networks (WANs). Such networking environments are commonplace in offices, enterprise-wide computer networks, intranets, and the Internet. It should be understood that any number of components shown in FIG. 1A may be employed within the computing environment 100 within the scope of the present invention. Each may be implemented via a single device or multiple devices cooperating in a distributed environment. Additionally, other components not shown may also be included within the environment. As such, it should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory.

Figure 1B:
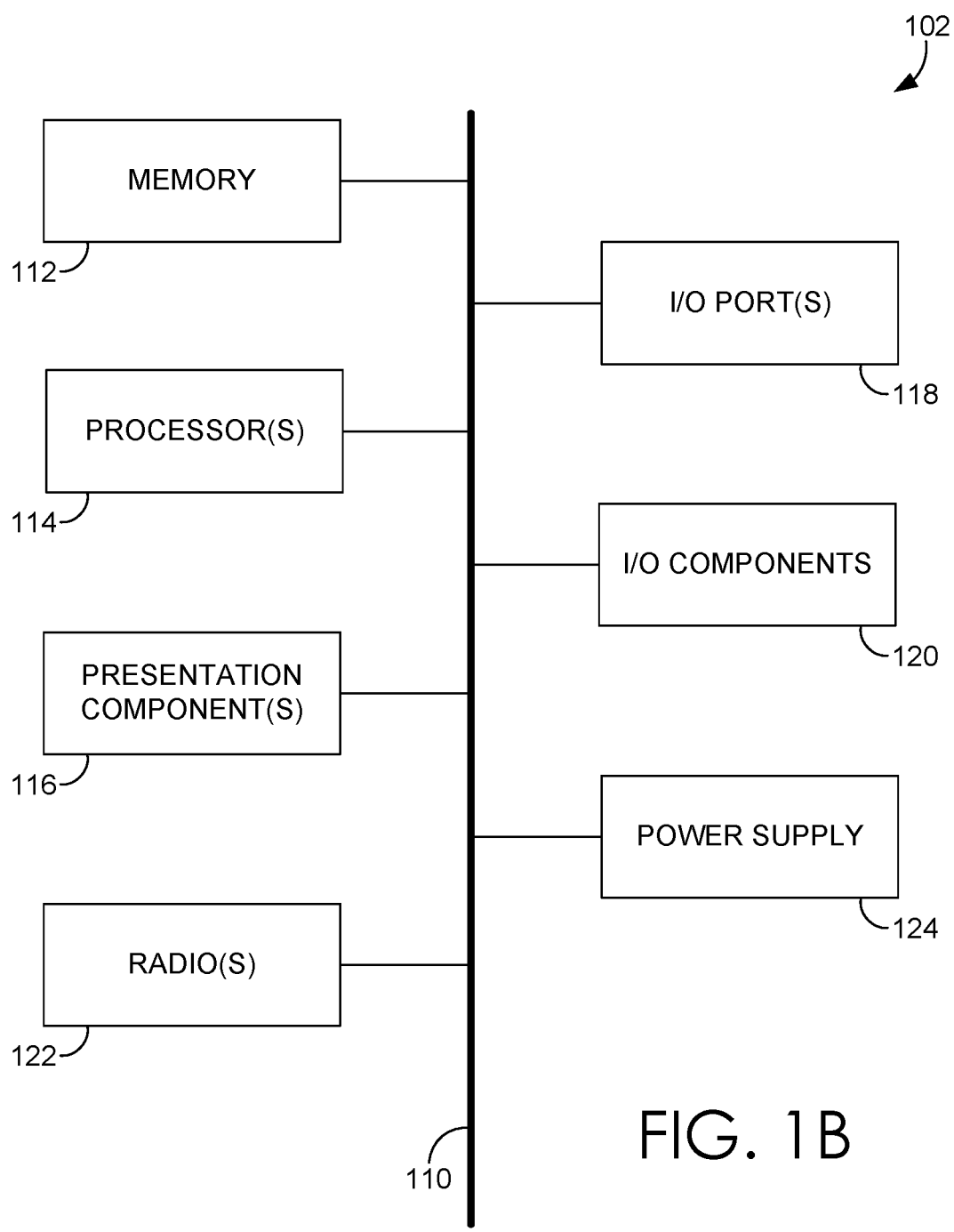

Turning to FIG. 1B, there is shown one example embodiment of the computing device 102. The computing device 102 includes a bus 110 that directly or indirectly couples one or more of the following components: memory 112, one or more processors 114, one or more presentation components 116, input/output (I/O) ports 118, input/output components 120, radio 122, and an illustrative power supply 124. Bus 110 represents what may be one or more busses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider the presentation components 116 to be an I/O component. Also, the one or more processors 114 may be couple to and/or be integrated with the memory 112. As such, the diagram of FIG. 1B is merely one example of the computing device 102 that can be used in connection with one or more embodiments of the present invention. Distinction is not made between such categories as "workstation," "server," "laptop," "hand-held device," etc., as all are contemplated within the scope of FIG. 1B and reference to "computing device."

The computing device 102 includes a variety of computer-readable media, in embodiments. Computer-readable media can be any available media that can be accessed by the computing device 102 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 102. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 112 includes computer-storage media in the form of volatile and/or nonvolatile memory. The memory 112 may be removable, non-removable, or a combination thereof. Examples of hardware components for memory include solid-state memory, hard drives, optical-disc drives, etc. The computing device 102 may include the one or more processors 114 that read data from the memory 112 and/or the I/O components 120. The presentation component(s) 116 present data indications to a user or other device. An example of the presentation component(s) 116 include a display device, speaker, printing component, vibrating component, etc.

In some embodiments, the computing device 102 may include one or more radio(s) 122 that facilitates communication with a wireless network. Illustrative wireless telecommunications technologies include CDMA, GPRS, TDMA, GSM, and the like, though embodiments are not limited to telecommunications networks. The radio(s) 122 may additionally or alternatively facilitate other types of wireless communications including Wi-Fi, WiMAX, LTE, or other VoIP communications. As can be appreciated, in various embodiments, the one or more radio(s) 122 can be configured to support multiple technologies and/or multiple radios can be utilized to support multiple technologies.

I/O ports 118 allow the computing device 102 to be logically coupled to other components, including I/O components 120, some of which may be built in to the computing device 102. Illustrative components include a microphone, joystick, game pad, satellite dish, scanner, printer, wireless device, etc. The I/O components 120 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing device 102. The computing device 102 may be equipped with depth cameras, such as stereoscopic camera systems, infrared camera systems, RGB camera systems, touchscreen technology, and combinations of these, for gesture detection and recognition. Additionally, the computing device 102 may be equipped with accelerometers or gyroscopes that enable detection of motion. Finally, the computing device 102 depicted in FIG. 1B is provided as one example of any number of suitable computers.

The computing device 102 may actually be a plurality of computing devices, in some embodiments. In various embodiments, the computing device 102 may include one or more software agents, an adaptive multi-agent operating system, or the like. It will be appreciated that the computing device 102 may take the form of an adaptive single agent system or a non-agent system, for example. The computing device 102 may be a distributed computing system of multiple remote computers, a data processing system, a centralized computing system, a networked computing system, or alternatively, may be a single computer such as a desktop or laptop computer.

Figure 2:
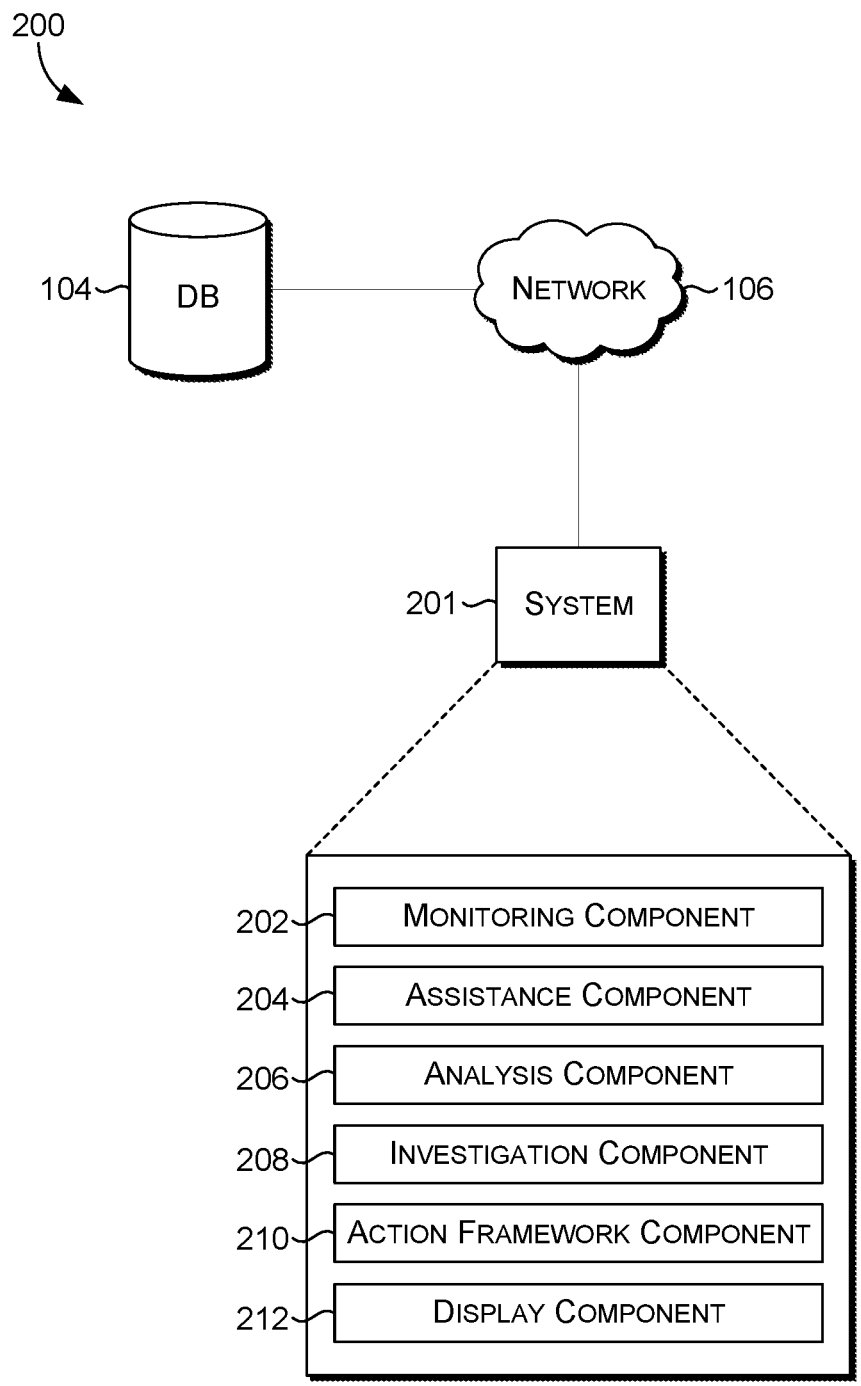
FIG. 2 illustrates a block diagram of an intelligent defect analysis system environment, in accordance with an embodiment of the disclosure.

Turning to FIG. 2, a block diagram of a system environment 200 is shown, which is used to conduct intelligent defect analysis within the computing environment 100 of FIG. 1, for example. The system environment 200 comprises one or more of the data store 104, the network 106, the one or more remote computers (not shown), and a defect analysis system 201, in various embodiments. Further, the defect analysis system 201 may comprise various combinations of a monitoring component 202, an assistance component 204, an analysis component 206, an investigation component 208, an action framework component 210, and/or a display component 212.

In some embodiments, the data store 104 is configured to store a plurality of historical records. For example, the data store 104 may act as a source device, which has be previously described hereinabove. The historical records can be associated with one or more previously detected system defects that have occurred, have been identified, have been categorized, and have been documented, for example, as having occurred within a client environment and/or in a production environment. Additionally, in some embodiments, the historical records are stored in association with previously identified keywords, wherein the keywords may be associated with and/or may correspond to one or more of the previously detected system defects. In embodiments, the data store 104 is configured to be in communication with the network 106, which is in turn configured to be in communication with the defect analysis system 201 and its components, as described hereinafter.

Figure 5:
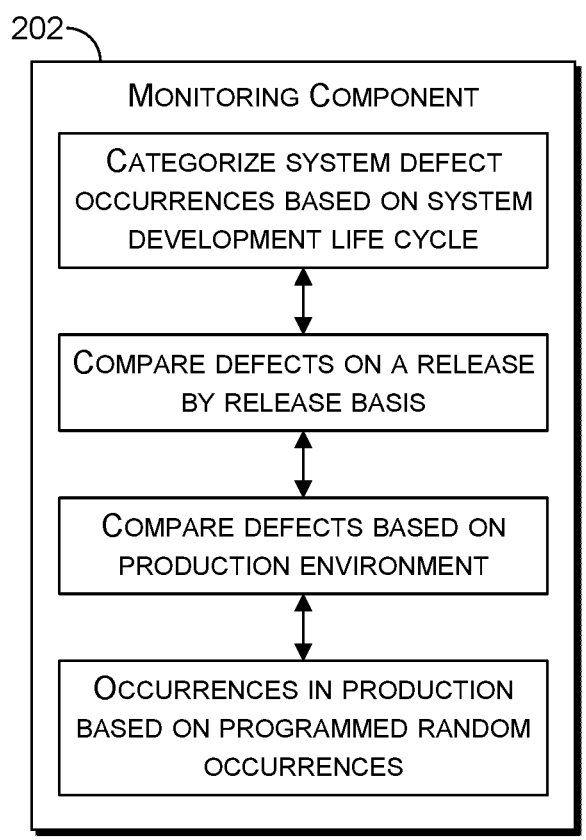
FIG. 5 illustrates a monitoring component of the defect analysis system of FIG. 2, in accordance with an embodiment of the present disclosure.

As stated above, the defect analysis system 201 is comprised of multiple components, in various embodiments. At least one of these components is the monitoring component 202, in embodiments. The monitoring component 202 is configured to periodically monitor the client environment, in some embodiments. In further embodiments, the monitoring component 202 is configured to periodically monitor the production environment. Further, the monitoring component 202 is configured to identify, for example, one or more system defects occurring within the client environment. In further embodiments, the monitoring component 202 monitors, tracks, identifies, and categorized each of a plurality of system defects that occur in a production and/or client environment. FIG. 5 illustrates further detail of an embodiment of the monitoring component 202. Particularly, the monitoring component 202 is configured to monitor system defects as they occur, arise in, or otherwise manifest within the client environment, wherein the monitoring can be performed in a multitude of ways. These monitoring component can monitor, track, and/or identify system defects using one or more methods, and can perform operations and functions such as, for example: categorizing each of many system defect occurrences based on a stage of a system development life cycle; comparing each of many system defects that occur based on a release-by-release basis; comparing defects based on the particular client or production environment; and monitoring occurrences in a production environment based on programmed random occurrences.

Figure 7:
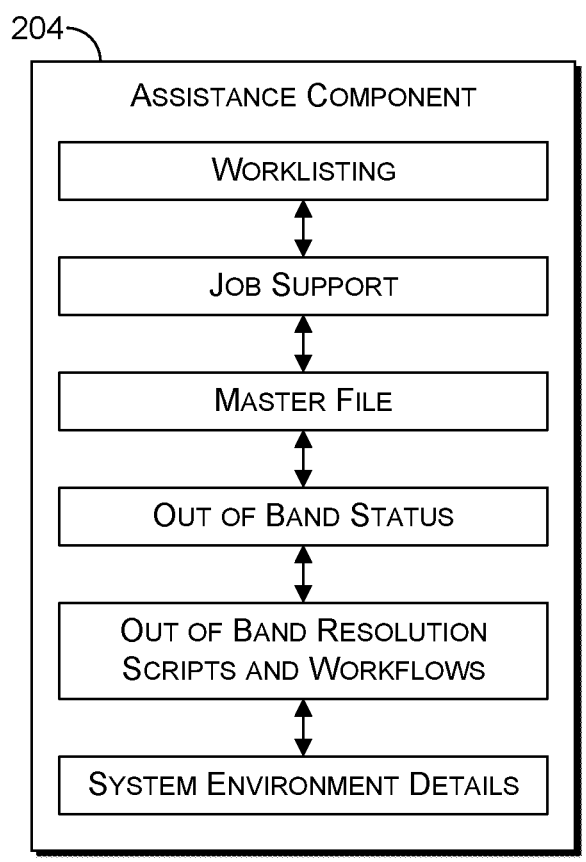
FIG. 7 illustrates an assistance component of the intelligent defect analysis system environment of FIGS. 1A and 1B, in accordance with an embodiment of the present disclosure.

In embodiments, the defect analysis system 201 is also comprised of the assistance component 204. FIG. 7 illustrates further detail of an embodiment of the assistance component 204. In some embodiments, the assistance component 204 can assist with repetitive and/or "well-defined" problems that are associated with and/or which correspond to known solutions. Specifically, the assistance component 204 can, in various embodiments, assist and/or perform functions related to work listing, job support, master files, out of band statuses, out of band resolution scripts and workflows, and issues with system environment details.

In additional embodiments, the assistance component 204 is configured to determine whether or not a system defect identified through monitoring is a well-defined problem. The assistance component 204 determines that a system defect can be categorized or identified as a well-known problem within the client environment when the problem has been detected a number of times greater than a predetermined threshold number of times. As such, the assistance component 204 can make a determination for each individual system defect of a plurality of system defects that are identified as occurring through monitoring of the client or production environment. Upon determining that the particular system defect is a well-defined problem and/or can be categorized as being a well-defined problem, the assistance component 204 generates a notification comprised of a user-interactive chatbot, in such embodiments. The user-interactive chatbot is configured to assist a user with identifying a solution to well-known problems by providing, automatically and in response to the determination of the assistance component 204, specific previously-utilized solutions that corrected, addressed, and/or which overcame prior occurrences of the same well-defined problem as the current system defect.

The defect analysis system 201 of FIG. 2 comprises an analysis component 206, in embodiments. The analysis component 206, in some embodiments, is configured to perform natural language processing that analyzes a system defect that has been identified by the monitoring component 202. Specifically, the natural language processing applied to the system defect can identify one or more keywords that are associated with the identified system defect, for example. In some embodiments, the analysis component 206 is further configured to identify one or more of a plurality of historical records stored in the data store 104 that are associated with the one or more keywords identified using the analysis of the current system defect.

Additionally, the defect analysis system 201 of FIG. 2 comprises an investigation component 208, in embodiments. The investigation component can identify, within the client environment, one or more criteria for a system defect and to identify when the one or more criteria are met or satisfied by the system defect. For example, if a particular keyword parsed from the system defect is associated with a solution that includes keywords of "a server which is down", the investigation component 208 can investigate, query, and determine whether or not the server accessed by the client environment is currently down and/or is not functioning. If the server is determined by the investigation component 208 to be up and functioning correctly, the investigation component 208 can eliminate a server being down as a cause of the current system defect, and can eliminate the solution associated with "server which is down" as a candidate solution for the current system defect, for example. By matching keywords parsed by the system defect to keywords in various solutions, the investigation component 208 can attempt to identify a solution for the system defect, and can rule out solutions that do not apply to the system defect, in embodiments. The investigation component 208 can utilize machine learning to continuously and dynamically learn from feedback and determine potential causes of system defects, or potential statuses which are not the cause of a defect.

Continuing, the defect analysis system 201 of FIG. 2 comprises an action framework component 210, in embodiments. In some embodiments, the action framework component 210 is configured to identify one or more solutions that are associated with the one or more of the plurality of historical records and are associated the one or more keywords identified from the system defect. Specifically, the action framework component can determine the steps needed to fix the identified defect.

Finally, the defect analysis system 201 may further comprise a display component 212, in some embodiments. The display component 212 is configured to cause display of a notification on a graphical user interface, wherein the notification includes at least one of the one or more keywords or the one or more solutions that are identified by the action framework component 210, as discussed above. In some embodiments, the display component 212 is also configured to receive a selection of the one or more keywords and/or the one or more solutions displayed. Based on receiving the selection, the display component 212 causes display of additional information associated with the selected keyword and/or solution. In further embodiments, the display component 212 is configured to display a notification in the form of an impact analysis report.

Figure 3:
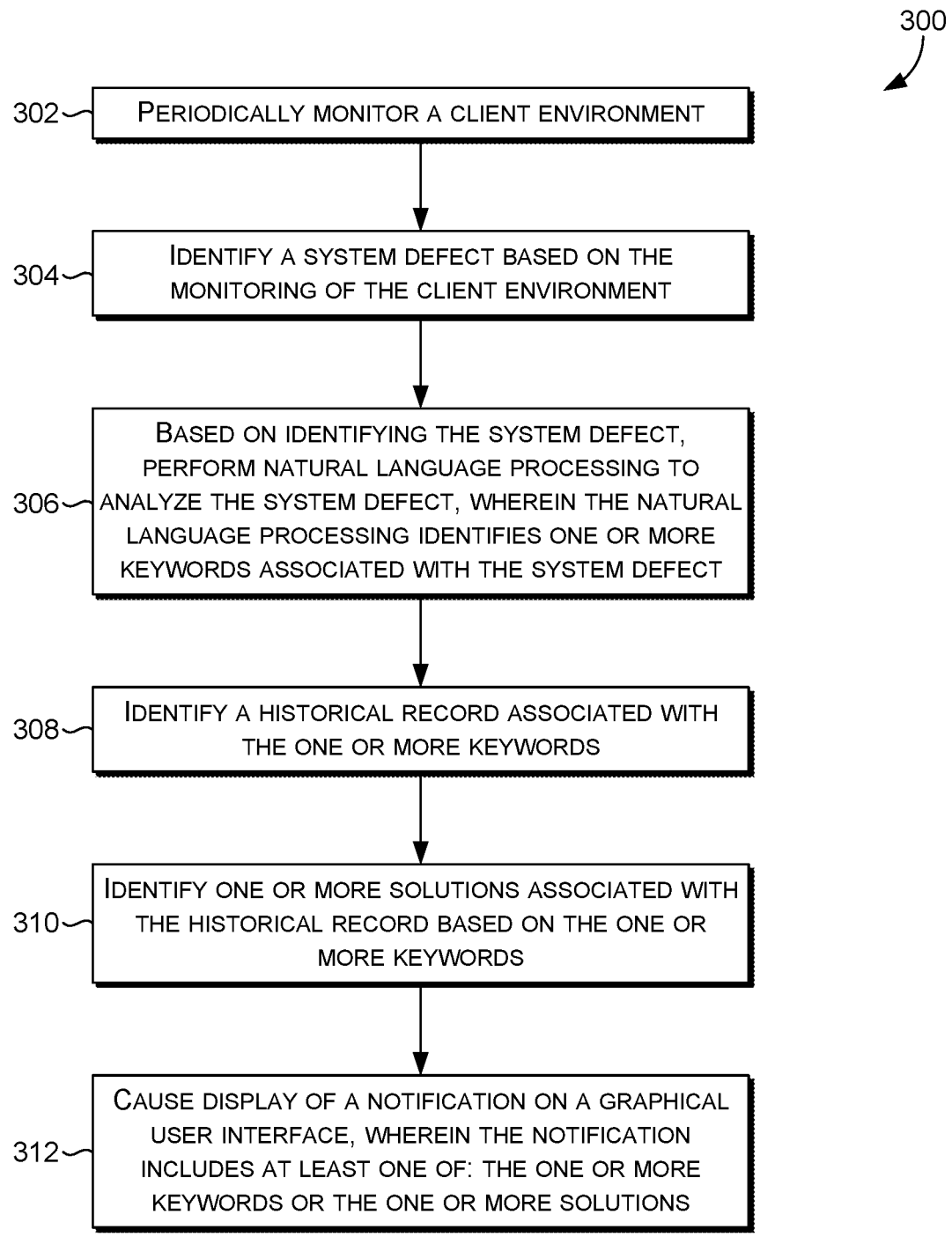
FIG. 3 illustrates a flow diagram of an method for conducting intelligent defect analysis, in accordance with an embodiment of the present disclosure.

FIG. 3 illustrates a flow diagram of an exemplary method 300 for intelligent defect analysis, in accordance with aspects of the present disclosure. It will be understood that each block of the flowcharts, and combinations of blocks in the flowcharts, may be implemented by various means, such as hardware, firmware, processor, circuitry, and/or other devices associated with execution of software including one or more computer program instructions. For example, one or more of the procedures described above may be embodied by computer program instructions. In this regard, the computer program instructions which embody the procedures described above may be stored by a memory of an apparatus employing an embodiment of the present invention and executed by a processor of the apparatus. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture, the execution of which implements the functions specified in the flowchart blocks. The computer program instructions may also be loaded onto a computer or other programmable apparatus to cause a series of operations to be performed on the computer or other programmable apparatus to produce a computer-implemented process such that the instructions executed on the computer or other programmable apparatus provide operations for implementing the functions specified in the flowchart blocks.

The operations illustrated in FIG. 3 may for example, be performed by the defect analysis system 201 of FIG. 2, and in this regard, the defect analysis system 201 may perform these operations through the use of one or more of processing elements, non-volatile memory, and volatile memory. It will be understood that the operating environment comprises a set of hardware components or hardware components coupled with software components configured to conduct intelligent defect analysis. These components may, for instance, utilize a processing element to execute operations, and may utilize non-volatile memory to store computer code executed by the processing element, as well as to store relevant intermediate or ultimate results produced from the system. It should be appreciated that, in some embodiments, the system may include a separate process, specially configured field programmable gate array (FPGA), or application specific interface circuit (ASIC) to perform its corresponding functions. In addition, computer program instructions and/or other type of code may be loaded onto a computer, processor or other programmable apparatus's circuitry to produce a machine, such that the computer, processor other programmable circuitry that execute the code on the machine create the means for implementing the various functions described in connection with the prediction system.

At block 302, the method 300 comprises periodically monitoring a client environment, for example, at reoccurring predetermined intervals. For example, the method could include monitoring the client environment once every hour, or monitoring the client environment each day at noon, central time. Additionally, in some embodiments, the client environment which is being periodically monitored can be an electronic health record system. The graphical user interface 600 displayed in FIG. 6 provides an example embodiment of a visual display of the output of the monitoring step. As shown in FIG. 6, the graphical user interface 600 includes rows and columns associated with particular clients, historical records, and payment systems. As an example, the numerals associated with hospital 14 can indicate that monitoring of the payment system has resulted in detecting a system defect.

At block 304, the method 300 comprises identifying a system defect based on the monitoring of the client environment. In some embodiments, the system defect identified is a predefined system defect which meets a threshold quantity of prior detections in the client environment. For example, when a threshold quantity of the same particular system defects has occurred, that particular system defect can be "defined" and used to identify subsequent system defects that occur, which are the same type or kind. In further embodiments, if the system defect that is identified by monitoring a payment system in a client environment is determined to be the same type and/or kind as a predefined system defect, a notification in the form of a chatbot can be displayed, where the notification displays predetermined information that is associated with and specific to the predefined system defect.

Based on identifying the system defect, at block 306, the method 300 comprises performing natural language processing to analyze the system defect, wherein the natural language processing identifies one or more keywords associated with the system defect. In some embodiments, the keywords can be identified from unstructured, free text obtained from the system defect that has been identified. In further embodiments, the text can be preprocessed such that the identified keywords can be matched with keywords located in previously-identified system defects, for example, as associated with historical records and/or previously employed solutions. In further embodiments, the keywords can be determined using intelligent natural language processing.

At block 308, a historical record that is associated with the one or more keywords is identified. In some embodiments, the historical record is an electronic health record. The method 300, at block 310, identifies one or more solutions associated with the historical record based on the one or more keywords. In some embodiments, the method further comprises identifying multiple keywords associated with the defect and further identifying additional historical records associated with the additional identified keywords. In further embodiments, the method additionally comprises storing, in a data store, the system defect in association with the identified keywords, or the identified solution.

Then, at block 312, a notification is caused to be displayed via a graphical user interface, wherein the notification includes at least one of: the one or more keywords and/or the one or more solutions. As discussed above, in some embodiments, the notification can be in the form of a user-interactive chat bot. Additionally, in some embodiments, a subsequent or additional selection of the one or more keywords and/or the one or more solutions is received, and based on this selection, additional information is displayed. In further embodiments, the method 300 further comprises displaying the notification in the form of an impact analysis report.

Figure 8:
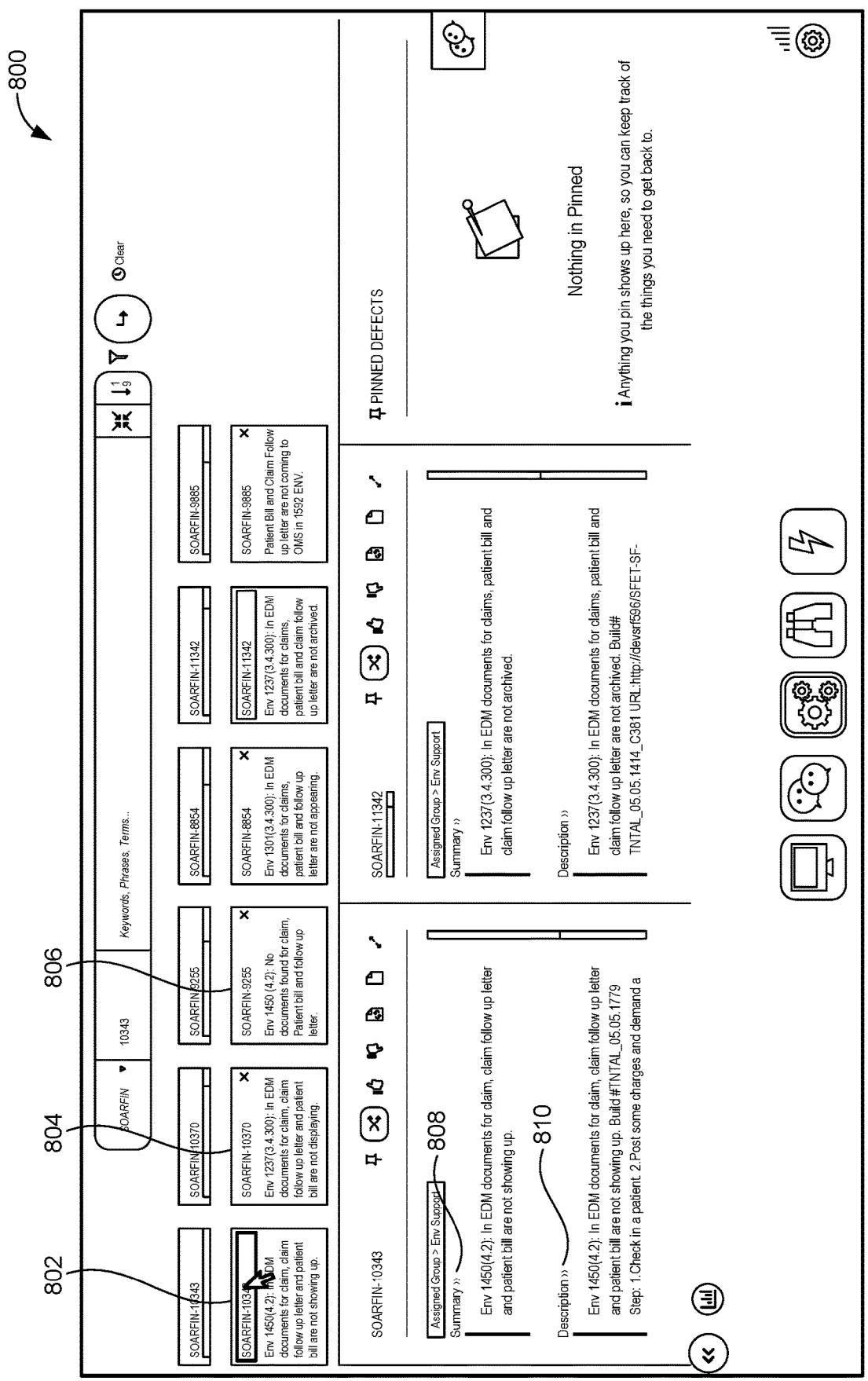
FIGS. 8-13 illustrate a plurality of graphical user interfaces that are responsive to user interactions with the defect analysis system of FIG. 2, in accordance with an embodiment of the present disclosure.
Figure 9:
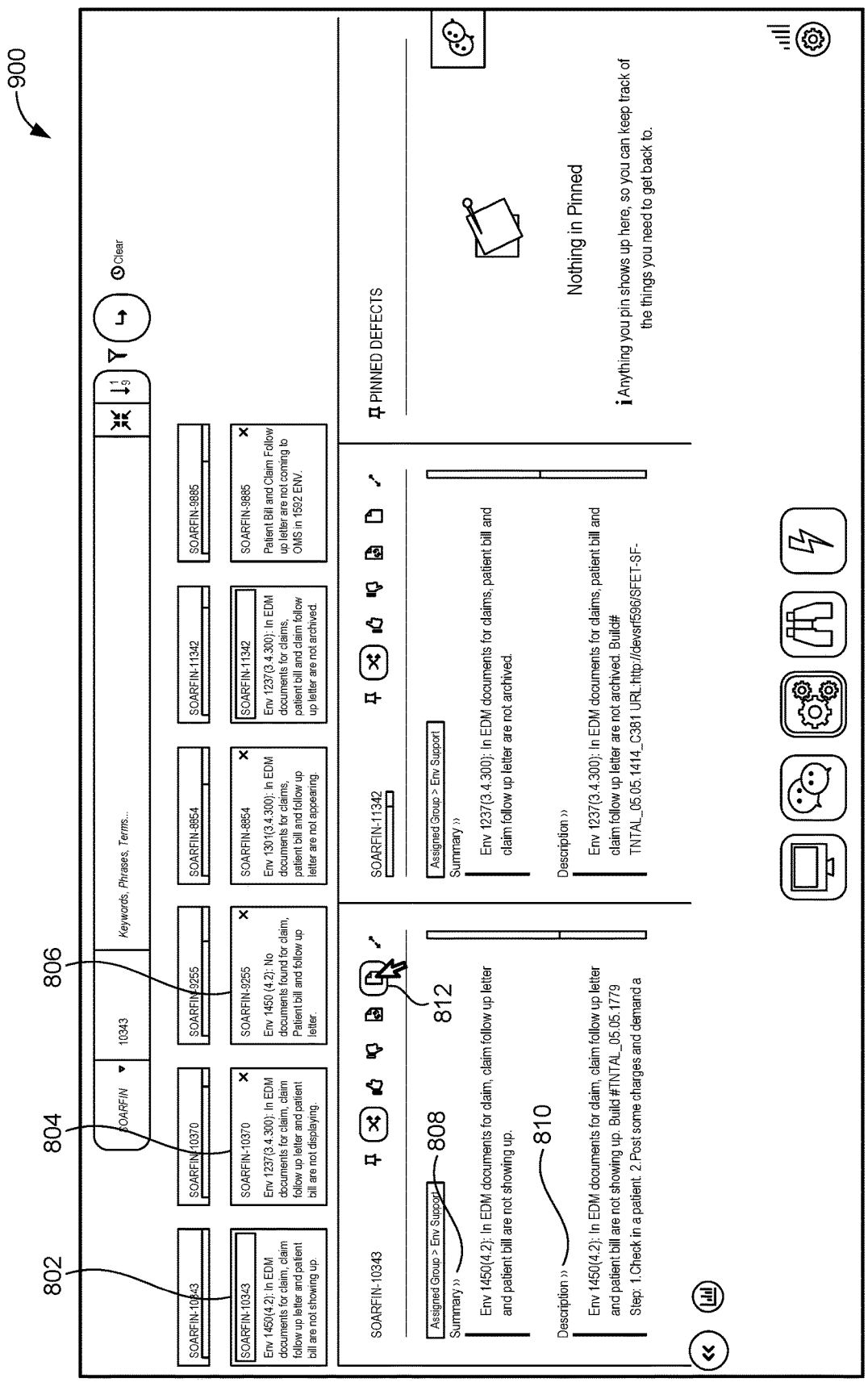
Figure 10:
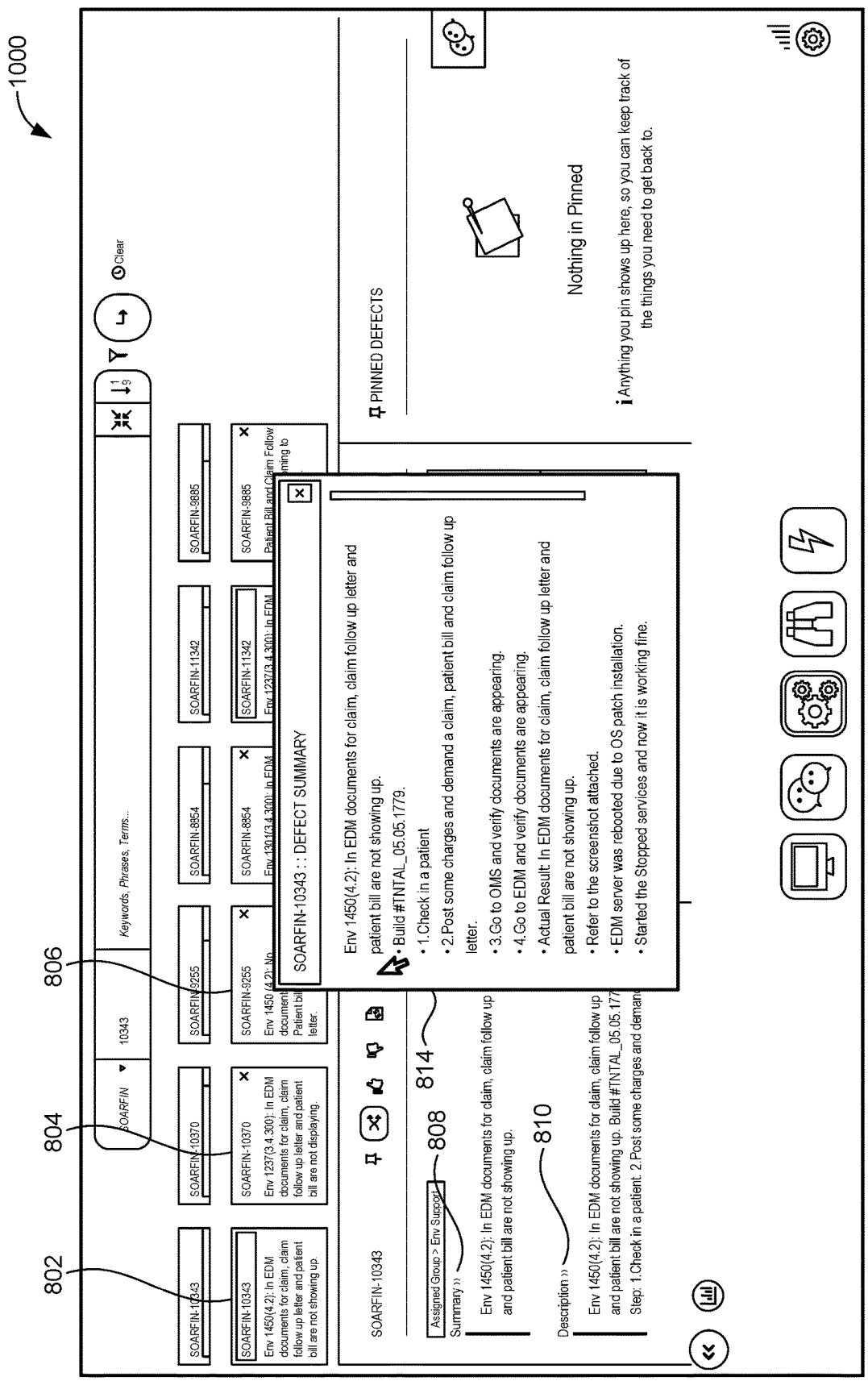

Turning to FIGS. 8-13, graphical user interfaces are provided in accordance with the aspects discussed herein. FIG. 8 provides a graphical user interface 800 that displays an impact analysis report. The impact analysis report can include system defects (e.g., first system defect 802, multiple system defects 804 and 806) that have been identified, the keywords displayed for example in pop-up windows 814 and 820 associated with those respective system defects, and allows for interaction by the user through selection of the system defects (e.g., first system defect 802, multiple system defects 804 and 806). Specifically, as seen by the position of the cursor in FIG. 8, a user may select a first system defect 802. As shown in FIG. 8, based on receiving selection of the first system defect 802, the graphical user interface 800 displays a summary 808 and description 810 of the first system defect 802. Additionally, the impact analysis report provides several selectable buttons associated with the displayed system defect information. FIG. 9 provides an example of a user selecting one of the selectable buttons from the graphical user interface 900, which displays sections and corresponding selectable buttons for each of one or more system defects being displayed. Based on receiving a selection of a detailed report button 812, the graphical user interface 1000, as shown in FIG. 10, displays a pop-up window 814 that is associated with the first system defect 802. The pop-up window 1002 is configured to provide an in-depth report of for the first system defect 802 and a solution identified for that first system defect 802.

Figure 11:
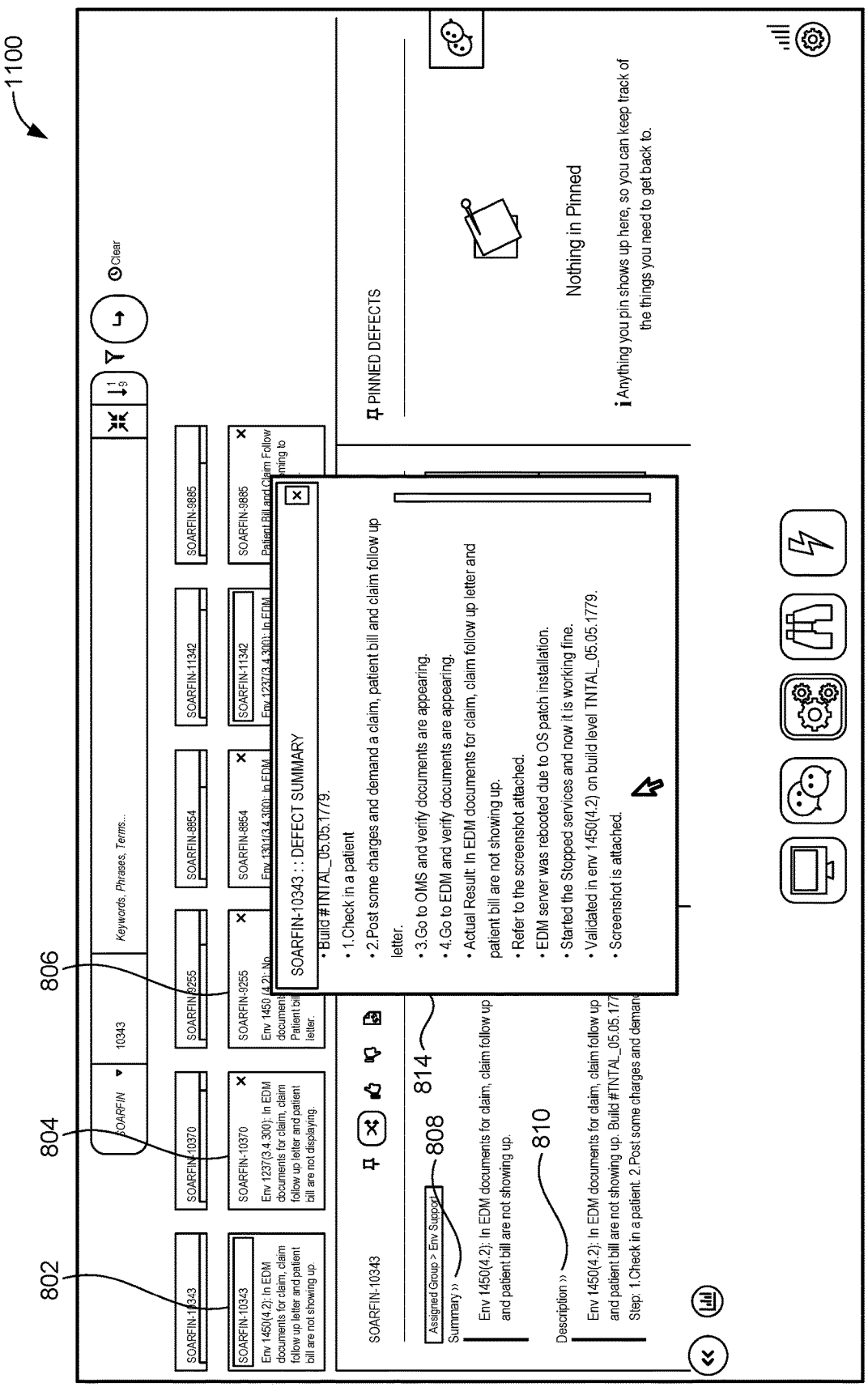
Figure 12:
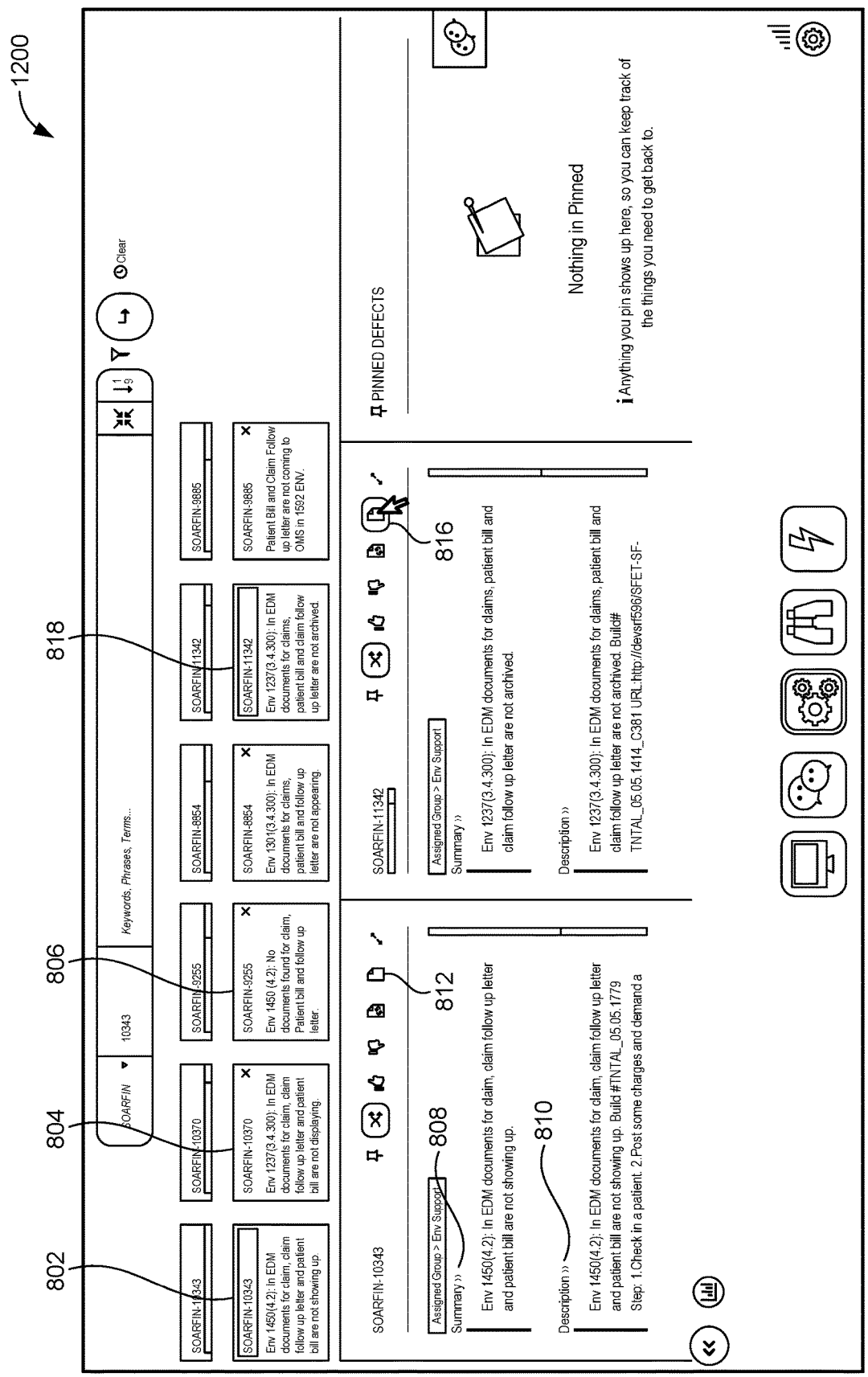
Figure 13:
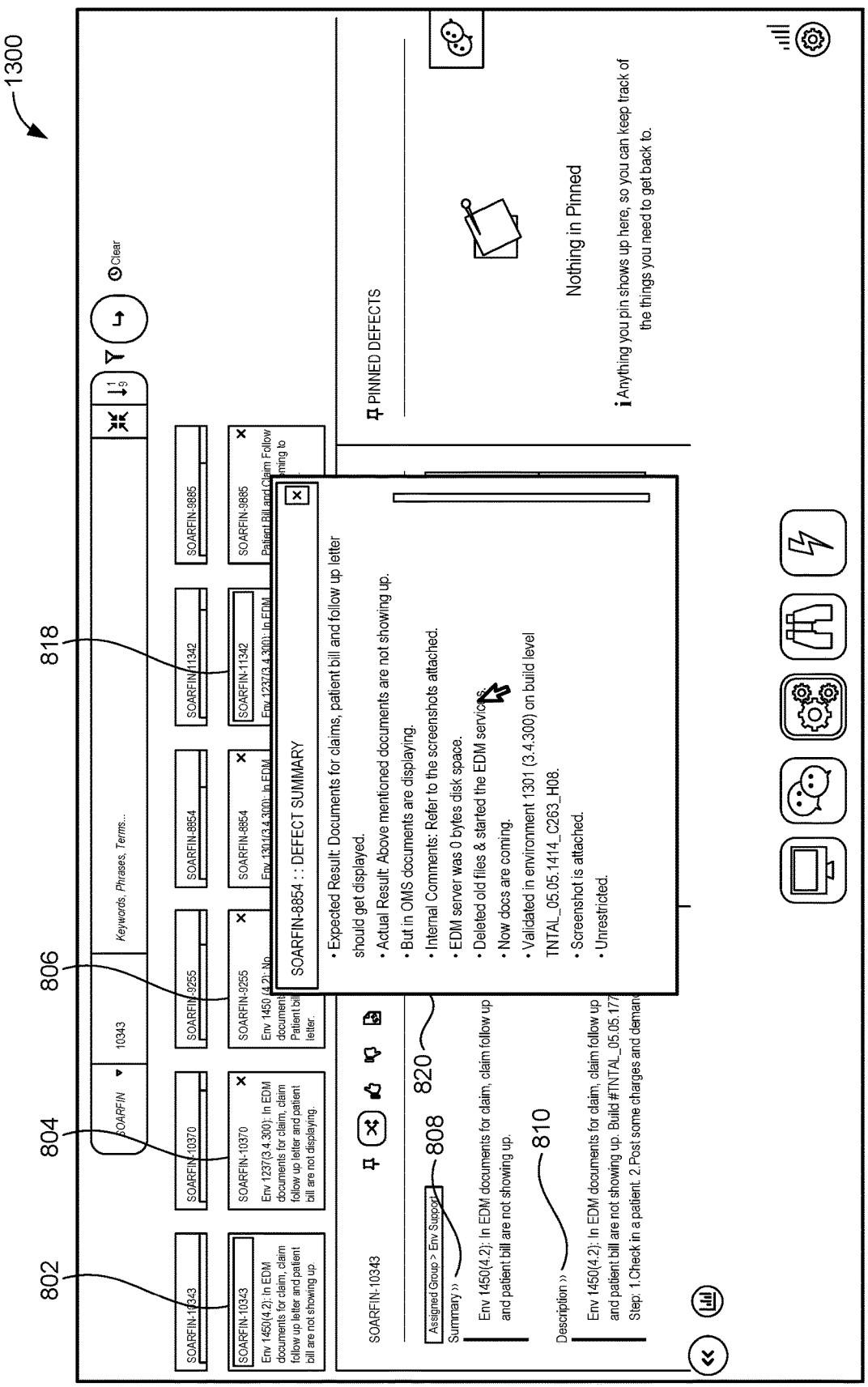

In further embodiments, the user may scroll through the information displayed in the pop-up window, as shown in the graphical user interface 1100 of FIG. 11. The user may then use the cursor to select the report button 816 associated with a second system defect 818 as shown in the graphical user interface 1200 of FIG. 12. This selection of the report button 816 causes the display of a pop-up window 820 associated with the second system defect 818, as shown in the graphical user interface of FIG. 13. As can be seen in each of FIGS. 10-13, the impact analysis report includes multiple additional features such as a search bar positioned at the top of the figure, and space for additional system defects to be pinned for future reference.

Figure 4:
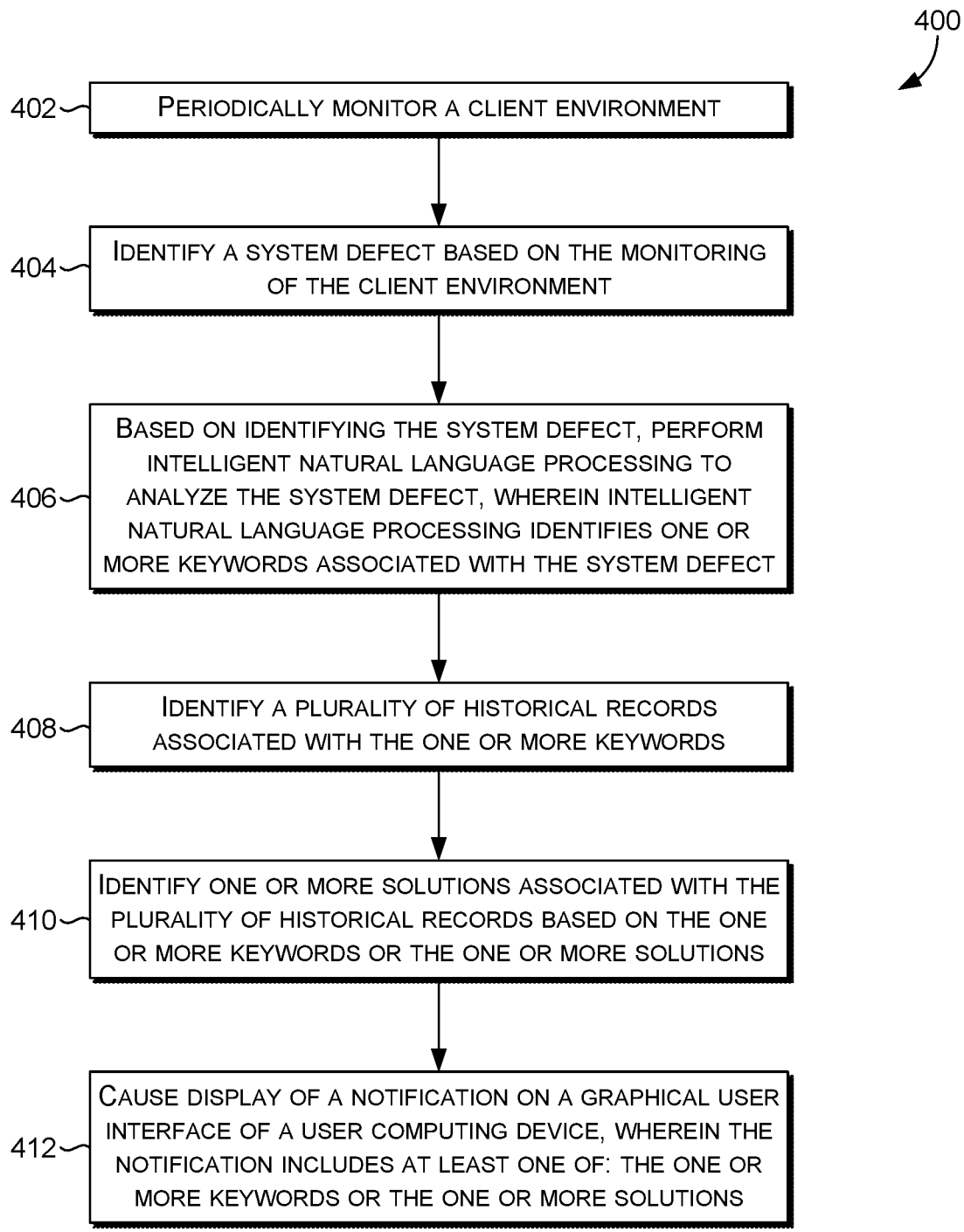
FIG. 4 illustrates a flow diagram of another method for conducting intelligent defect analysis, in accordance with an embodiment of the present disclosure.

Finally, FIG. 4 illustrates a flow diagram which describes one or more non-transitory computer-storage media having computer executable instructions embodied thereon that, when executed, perform a method for using the defect analysis system 201 of FIG. 2 to perform intelligent defect analysis. At block 402, the intelligent defect analysis system periodically monitors a client environment for potential defects. At block 404, the system identifies a system defect based on the periodic monitoring of the client environment. Next, based on identifying the defect, at block 406, the system performs intelligent natural language processing to analyze the system defect, wherein the intelligent natural language processing identifies one or more keywords associated with the system defect. Once the defects are analyzed, the system, at block 408, identifies a plurality of historical records associated with the one or more keywords. At block 410, the system identifies one or more solutions associated with the plurality of historical records based on the one or more keywords or the one or more solutions. Once the historical records are identified, the system, at block 412, causes display of a notification on a graphical user interface of a user computing device, wherein the notification includes at least one of: the one or more keywords or the one or more solutions.

The present invention has been described in relation to particular embodiments, which are intended in all respects to be illustrative rather than restrictive. Further, the present invention is not limited to these embodiments, but variations and modifications may be made without departing from the scope of the present invention.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations.

The invention claimed is:

1. A computer-implemented method for providing intelligent defect analysis, the method comprising:
    periodically monitoring a client environment;
    identifying a system defect, which includes unstructured, free text, based on the monitoring of the client environment;
    categorizing the system defect with a stage of a development life cycle of the client environment the system defect exists within, wherein the stage is associated with one or more build levels associated with the client environment;
    based on identifying and categorizing the system defect, performing natural language processing to analyze the system defect, wherein the natural language processing identifies, based on the unstructured, free text obtained from the system defect that has been identified, one or more keywords associated with the system defect;

identifying a historical record associated with the one or more keywords and the categorizing of the system defect;

identifying one or more configuration solutions for the client environment associated with the historical record based on the one or more keywords;

automatically adjusting a graphical user interface to display a notification to a user relating to the one or more configuration solutions on the graphical user interface, wherein the notification comprises a user-interactive chatbot which automatically displays the historic record that is related to the one or more solutions for the system defect;

generating an interactable link, by the user-interactive chatbot, which, in response to an interaction, displays the one or more historic solutions related to the system defect;

increasing a space of the graphical user interface to display additional system defects to be displayed for future reference, wherein the additional system defects are associated with the system defect;

displaying, by the graphical user interface, the additional system defects including an associated build level for each of the additional system defects;

receiving an input via the graphical user interface related to the one or more configuration solutions;

causing the one or more configuration solutions to be mapped to one or more executable steps;

automatically executing the executable steps to resolve the one or more configuration solutions;

generating an impact report identifying one or more potential system defects in the client environment related to the system defect; and generating a recommendation to resolve the one or more potential system defects.

2. The method of claim 1, wherein the client environment is periodically monitored at reoccurring predetermined intervals.

3. The method of claim 1, wherein the client environment is an electronic health record system, and wherein the historical record is associated with one or more electronic health records.

4. The method of claim 1, wherein the system defect is a predefined defect that meets a threshold quantity of prior detections in the client environment.

5. The method of claim 1, wherein the notification comprises an impact analysis report, and wherein the impact analysis report includes a summary of the system defect identified.

6. The method of claim 5, wherein the method further comprises:
receiving a selection of the one or more keywords or the one or more configuration solutions that are included in the notification; and
in response to the selection, causing display of the historical record associated with the one or more keywords or the one or more configuration solutions.

7. The method of claim 1, further comprising:
identifying one or more additional keywords, stored in a database, that match or partially match the one or more keywords associated with the system defect,
wherein the one or more configuration solutions are further identified based on the one or more additional keywords.

8. The method of claim 1, further comprising:
identifying one or more additional system defects, stored in a database, that match or partially match the system defect,
wherein the one or more configuration solutions are further identified based on the one or more additional keywords.

9. The method of claim 1, further comprising:
identifying an additional system defect that is a match or partial match to the system defect identified,
wherein the one or more configuration solutions are further identified based on the additional system defect that is a match or partial match.

10. The method of claim 1, wherein the method further comprises:
storing, in a database, the system defect in association with at least one of the one or more keywords or the one or more configuration solutions.

11. The method of claim 1, wherein identifying the system defect based on the monitoring of the client environment comprises using a trained machine learning model to identify the system defect.

12. The method of claim 1, wherein displaying the notification further comprises:
displaying the one or more build levels associated with the system defect; and
displaying the one or more additional system defects in the space of the graphical user interface as interactable elements.

13. One or more non-transitory computer-storage media having computer-executable instructions embodied thereon that, when executed, perform a method of providing intelligent defect analysis, the instructions comprising:
periodically monitoring a client environment;
identifying a system defect, which includes unstructured, free text, based on the monitoring of the client environment;
categorizing the system defect with a stage of a development life cycle of the client environment the system defect exists within, wherein the stage is associated with one or more build levels associated with the client environment;
based on identifying and categorizing the system defect, performing natural language processing to analyze the system defect, wherein the natural language processing identifies, based on the unstructured, free text obtained from the system defect that has been identified, one or more keywords associated with the system defect;
identifying a historical record associated with the one or more keywords and the categorizing of the system defect;
identifying one or more configuration solutions for the client environment associated with the historical record based on the one or more keywords;
automatically adjusting a graphical user interface to display a notification to a user relating to the one or more configuration solutions on the graphical user interface, wherein the notification comprises a user-interactive chatbot which automatically displays the historic record that is related to the one or more solutions for the system defect;
generating an interactable link, by the user-interactive chatbot, which, in response to an interaction, displays the one or more historic solutions related to the system defect;
increasing a space of the graphical user interface to display additional system defects to be displayed for future reference, wherein the additional system defects are associated with the system defect;

displaying, by the graphical user interface, the additional system defects including an associated build level for each of the additional system defects;

receiving an input via the graphical user interface related to the one or more configuration solutions;

causing the one or more configuration solutions to be mapped to one or more executable steps;

automatically executing the executable steps to resolve the one or more configuration solutions;

generating an impact report identifying one or more potential system defects in the client environment related to the system defect; and generating a recommendation to resolve the one or more potential system defects.

14. The media of claim 13, wherein the client environment is an electronic health record system, wherein the plurality of historical records are associated with electronic health records in the electronic health record system, and wherein the plurality of historical records are pre-processed using intelligent natural language processing to identify one or more previously-documented keywords, solutions, or system defects in the client environment.

15. The media of claim 14, wherein identifying the one or more configuration solutions associated with the plurality of historical records is further based on the one or more previously-documented keywords, solutions, or system defects in the client environment.

16. The media of claim 13, wherein the client environment is investigated, via a processor, to determine when one or more potential causes of the system defect identified are present.

17. The media of claim 16, wherein when a first potential cause in the one or more potential causes is determined to be absent in the client environment, determining not to display a first solution of the one or more configuration solutions, wherein the first solution is omitted as being associated with the first potential cause that is absent in the client environment.

18. The media of claim 13, wherein the instructions further comprise:

receiving a selection of at least one of the one or more keywords or the one or more configuration solutions; and displaying at least one of the plurality of historical records identified as associated with the one or more keywords or the one or more configuration solutions that are associated with the system defect.

19. A system for providing intelligent defect analysis, the system comprising:

a hardware processor configured to perform operations in response to receiving an instruction selected from a predefined native instruction set of codes;

a memory;

a database configured to store a plurality of historical records;

a proactive monitoring component configured to:

periodically monitor a client environment;

identify a system defect, which includes unstructured, free text, based on the monitoring of the client environment;

categorize the system defect with a stage of a development life cycle of the client environment the system defect exists within, wherein the stage is associated with one or more build levels associated with the client environment;

based on identifying and categorizing the system defect, perform natural language processing to analyze the system defect, wherein the natural language processing identifies, based on the unstructured, free text obtained from the system defect that has been identified, one or more keywords associated with the system defect;

identify a historical record associated with the one or more keywords and the categorizing of the system defect;

identify one or more configuration solutions for the client environment associated with the historical record based on the one or more keywords;

automatically adjust a graphical user interface to display a notification to a user relating to the one or more configuration solutions on the graphical user interface, wherein the notification comprises a user-interactive chatbot which automatically displays the historic record that is related to the one or more solutions for the system defect;

generate an interactable link, by the user-interactive chatbot, which, in response to an interaction, displays the one or more historic solutions related to the system defect;

increase a space of the graphical user interface to display additional system defects to be displayed for future reference, wherein the additional system defects are associated with the system defect;

display, by the graphical user interface, the additional system defects including an associated build level for each of the additional system defects;

receive an input via the graphical user interface related to the one or more configuration solutions;

cause the one or more configuration solutions to be mapped to one or more executable steps;

automatically execute the executable steps to resolve the one or more configuration solutions;

generate an impact report identifying one or more potential system defects in the client environment related to the system defect; and generate a recommendation to resolve the one or more potential system defects.

20. The system of claim 19, wherein the database is further configured to:

store the system defect in association with at least one of the one or more keywords or the one or more configuration solutions.

* * * * *